US010156534B2

United States Patent
Tuller et al.

(10) Patent No.: US 10,156,534 B2
(45) Date of Patent: Dec. 18, 2018

(54) GAS SENSOR WITH TIN MONOXIDE DISKS

(71) Applicants: MASSACHUSETTS INSTITUTE OF TECHNOLOGY, Cambridge, MA (US); UNIVERSIDADE ESTADUAL PAULISTA, Sao Paulo (BR)

(72) Inventors: Harry L. Tuller, Wellesley, MA (US); Pedro Henrique Suman, Araraquara (BR); Anderson Andre Felix, Araraquara (BR); Jose Arana Varela, Araraquara (BR); Marcelo Ornaghi Orlandi, Sao Carlos (BR)

(73) Assignee: Massachusetts Institute of Technology, Cambridge, MA (US)

( * ) Notice: Subject to any disclaimer, the term of this patent is extended or adjusted under 35 U.S.C. 154(b) by 113 days.

(21) Appl. No.: 14/889,994

(22) PCT Filed: May 15, 2014

(86) PCT No.: PCT/US2014/038158
§ 371 (c)(1),
(2) Date: Nov. 9, 2015

(87) PCT Pub. No.: WO2014/189758
PCT Pub. Date: Nov. 27, 2014

(65) Prior Publication Data
US 2016/0146749 A1    May 26, 2016

Related U.S. Application Data

(60) Provisional application No. 61/825,603, filed on May 21, 2013.

(51) Int. Cl.
G01N 27/04 (2006.01)
G01N 33/00 (2006.01)

(52) U.S. Cl.
CPC .......... G01N 27/04 (2013.01); G01N 27/041 (2013.01); G01N 33/0036 (2013.01)

(58) Field of Classification Search
None
See application file for complete search history.

(56) References Cited

U.S. PATENT DOCUMENTS 4,169,369 A   10/1979   Chang
4,287,751 A   9/1981   Yasuda et al.

FOREIGN PATENT DOCUMENTS

WO   2010026985 A1   3/2010

OTHER PUBLICATIONS

Dai, Z. et al. Growth and Structure Evolution of Novel Tin Oxide Diskettes. J. Am. Chem. Soc., 2002, 124 (29), pp. 8673-8680.*
Batzill, Matthias et al. The Surface and Materials Science of Tin Oxide. Progress in Surface Science 79 pp. 47-154. 2005.*

(Continued)

*Primary Examiner* — Paul West
*Assistant Examiner* — Mark A Shabman
(74) *Attorney, Agent, or Firm* — Gesmer Updegrove LLP (57) ABSTRACT

Gas sensor. The sensor is a single crystalline SnO disk and circuitry for measuring electrical resistance of the disk is provided. A change in resistance in the disk indicates adsorption of a gas on the disk's surface. The sensor is particularly adapted for detecting $NO_2$ with high sensitivity and selectivity.

3 Claims, 6 Drawing Sheets

(56) References Cited

OTHER PUBLICATIONS

International Preliminary Report on Patentability dated Dec. 3, 2015 in connection with corresponding PCT Application No. PCT/US14/038158.
Wang, "Nanobelts, Nanowires, and Nanodiskettes of Semiconducting Oxides—From Materials to Nanodevices" Advanced Materials, vol. 15, No. 5, Mar. 7, 2003 pp. 432-436.
International Search Report and Written Opinion dated Aug. 6, 2014, in connection with PCT Application No. PCT/US2014/038158.
N.O. Korolkoff, Survey of toxic gas sensors and monitoring systems, Solid State Tech. 32 (1989) 49-64.
G. Weinmayr, E. Romeo, M. Sario, S. K. Weiland, F. Forastiere, Short-Term effects of PM10 and NO2 on respiratory health among children with asthma or asthma-like symptoms: a systematic review and meta-analysis, Environmental Health Perspectives 118 (2010) 449-457.
C. Pijolat, C. Pupier, M. Sauvan, G. Tournier, R. Lalauze, Gas detection for automotive pollution control, Sens. Actuators, B: Chem. 59 (1999) 195-202.
N. Yamazoe, N. Miura, Environmental gas-sensing, Sens. Actuators, B: Chem. 20 (1994) 95-102.
L. Zhang, J. Zhao, H. Lu, L. Li, J. Zheng, H. Li, Z. Zhu, Facile synthesis and ultrahigh ethanol response of hierarchically porous ZnO nanosheets, Sens. Actuators, B: Chem. 161 (2012) 209-215.
S. J. Kim, I. S. Hwang, C. W. Na, I. D. Kim, Y. C. Kang, J.H. Lee, Ultrasensitive and selective C2H5OH sensors using Rh-loaded In2O3 hollow spheres, J. Mat. Chem. 21 (2011) 18560-18567.
A. Gurlo, M. Ivanovskaya, N. Barsan, M. Schweizer-Berberich, U. Weimar, W. Gopel, A. Dieguez, Grain size control in nanocrystalline In2O3 semiconductor gas sensors, Sens. Actuators, B: Chem. 44 (1997) 327-333.
J. Tamaki, T. Hashishin, Y. Uno, D. V. Dao, S. Sugiyama, Ultrahigh-sensitive WO3 nanosensor with interdigitated Au nano-electrode for NO2 detection, Sens. Actuators, B: Chem. 132 (2008) 234-238.
I.-D. Kim, A. Rothschild, B. H. Lee, D. Y. Kim, S. M. Jo, H. L. Tuller, Ultrasensitive chemiresistors based on electrospun TiO2 nanofibers, Nano Lett. 6 (2006) 2009-2013.
D. D. Vuong, G. Sakai, K. Shimanoe, N.Yamazoe, Hydrogen sulfide gas sensing properties of thin films derived from SnO2 sols different in grain size, Sens. Actuators, B: Chem. 105 (2005) 437-442.
X. Han, M. Jin, S. Xie, Q. Kuang, Z. Jiang, Y. Jiang, Z. Xie, L. Zheng, Synthesis of tin dioxide octahedral nanoparticles with exposed high-energy {221} facets and enhanced gas-sensing properties, Angew. Chem. Int. Ed. 48 (2009) 9180-9183.
H.-C. Chiu, C.-S. Yeh, Hydrothermal synthesis of SnO2 nanoparticles and their gas-sensing of alcohol, J. Phys. Chem. C 111 (2007) 7256-7259.
Y. Kwak, J. Wang, S. Meang, G.-H. Kim, Hydrogen sensing properties of dielectrophoretically assembled SnO2 nanoparticles on CMOS-compatible micro-hotplates, Nanotechnology 22 (2011) 445501.
T. Hyodo, N. Nishida, Y. Shimizu, M. Egashira, Preparation and gas-sensing properties of thermally stable mesoporous SnO2 Sens. Actuators, B: Chem. 83 ( 2002) 209-215.
N. G. Cho, D. J. Yang, M. J. Jin, H. G. Kim, H. L. Tuller, I.-D. Kim, Highly sensitive SnO2 hollow nanofiber-based NO2 gas sensors, Sens. Actuators, B: Chem. 160 (2011) 1468-1472.
T. Hyodo, K. Sasahara, Y. Shimizu, M. Egashira, Preparation of macroporous SnO2 films using PMMA microspheres and their sensing properties to NOx and H2, Sens. Actuators, B: Chem. 106 (2005) 580-590.
J. Zhang, X. H. Liu, S. H. Wu, M. J. Xu, X. Z. Guo, S. R. Wang, Au nanoparticle-decorated porous SnO2 hollow spheres: a new model for a chemical sensor, J. Mat. Chem. 20 (2010) 6453-6459.
J.-A, Park, J. Moon, S.-J. Lee, S. H. Kim, H. Y. Chu, T. Zyung, SnO2—ZnO hybrid nanofibers-based highly sensitive nitrogen dioxides sensor, Sens. Actuators, B: Chem. 145 (2010) 592-595.
N. G. Cho, G. C. Whitfield, D. J. Yang, H.-G, Kim, H. L. Tuller, I.-D. Kim, Facile synthesis of Pt-functionalized SnO2 hollow hemispheres and their gas sensing properties, J. Electrochem. Soc. 157 (2010) J435-J439.
D.-J. Yang, I. Kamienchick, D. Y. Youn, A. Rothschild, I.-D. Kim, Ultrasensitive and highly selective gas sensors based on electrospun SnO2 nanofibers modified by Pd loading, Adv. Funct. Mater. 20 (2010) 4258-4264.
Z. Ling, C. Leach, R. Freer, NO2 sensitivity of a heterojunction sensor based on WO3 and doped SnO2, J. Eur. Ceram. Soc. 23 (2003) 1881-1891.
M. K. Verma, V. Gupta, A highly sensitive SnO2—CuO multilayered sensor structure for detection of H2S gas, Sens. Actuators, B: Chem. 166 (2012) 378-385.
Z. R. Dai, Z. W. Pan, Z. L. Wang, Growth and structure evolution of novel tin oxide diskettes, J. Am. Chem. Soc. 124 (2002) 8673-8680.
M. O. Orlandi, A. J. Ramirez, E. R. Leite, E. Longo, Morphological evolution of tin oxide nanobelts after phase transition, Cryst. Growth Des. 8 (2008) 1067-1072.
M. Batzil, U. Diebold, The surface and materials science of tin oxide, Progress in Surf. Sci. 79 (2005) 45-154.
Y. Ogo, H. Hiramatsu, K. Nomura, H. Yanagi, T. Kamiya, M. Hirano, H. Hosono, p-channel thin-film transistor using p-type oxide semiconductor, SnO, Appl. Phys. Lett. 93 (2009) 032113.
M. O. Orlandi, E. R. Leite, R. Aguiar, J. Bettini, E. Longo, Growth of SnO nanobelts and dendrites by a self-catalytic VLS process, J. Phys. Chem. B 110 (2006) 6621-6625.
P. H. Suman, M. O. Orlandi, Influence of processing parameters on nanomaterials synthesis efficiency by a carbothermal reduction process, J. Nanoparticle Research 13 (2011) 2081-2088.
S. Brunauer, P. H. Emmett; E. Teller. Adsorption of gases in multimolecular layers, J. Am. Chem. Soc. 60 (1938) 309-319.
J. L. G. Fierro, Metal Oxide Chemistry and Applications, CRC Press, Boca Raton, FL, 2006. ISBN 978-0824723712.
H.W. Ha and S.J. Hwang. Improvement of electrochemical performance of tin dioxide negative electrode materials upon cobalt substitution, Electrochimica Acta 55 (2010) 2841-2847.
U.S. Environmental Protection Agency: National Ambient Air Quality Standards (NAAQS). http://www.epa.gov/air/criteria.html.
M. Epifani, J. D. Prades, E. Comini, E. Pellicer, M. Avella,P. Siciliano, G. Faglia, A. Cirera, R. Scotti, F. Morazzoni, J.R. Morante. The role of surface oxygen vacancies in the NO2 sensing properties of SnO2 nanocrystals, J. Phys. Chem. C 112 (2008) 19540-19546.
Y.-E. Chang, D.-Y. Youn, G. Ankonina, D.-J. Yang, H.-G. Kim, A. Rothschild, I.-D. Kim, Fabrication and gas sensing properties of hollow SnO2 hemispheres, Chem. Commun. 27 (2009) 4019-4021.
K. Sahner, H. Tuller, Novel deposition techniques for metal oxide: prospects for gas sensing, J. Electroceram. 24 (2010) 177-199.
N. Barsan, U. Weimar, Conduction model of metal oxide gas sensors, J. Electroceram, 7 (2001) 143-167.
C. Xu, J. Tamaki, N. Miura, and N. Yamazoe, Grain-size effects on gas sensitivity of porous SnO2-based elements, Sens. Actuators B: Chem. 3 (1991) 147-155.
H. Keskinen, A. Tricoli, M. Marjamäki, J.M. Mäkelä, S.E. Pratsinis, Size-selected agglomerates of SnO2 nanoparticles as gas sensors, J. Appl. Phys. 106 (2009) 084316.
L. Shi and H. Lin, Preparation of band gap tunable SnO2 nanotubes and their ethanol sensing properties, Langmuir 27 (2011) 3977-3981.
A. Rothschild and Y. Komem, The effect of grain size on the sensitivity of nanocrystalline metal-oxide gas sensors, J. Appl. Phys. 95 (2044) 6374-6380.
D. Le Bellac, J.M. Kiat, P. Garnier, Electronic Ione pair localization and electrostatic energy calculations: application to α-PbO, SnO, Pb1-x(TiO)xO, Pb3O4, Pb3(V,P)2O8, and a BiSrCaCuO-type superconductor, J. Solid State Chem. 114 (1995) 459-468.
A. Walsh, G.W. Watson, Electronic structures of rocksalt, litharge, and herzenbergite SnO by density functional theory, Phys. Rev. B. 70 (2004) 235114.

* cited by examiner

GAS SENSOR WITH TIN MONOXIDE DISKS

PRIORITY INFORMATION

This application claims priority to U.S. provisional application Ser. No. 61/825,603 filed on May 21, 2013, the contents of which are incorporated herein by reference in their entirety.

BACKGROUND OF THE INVENTION

This invention relates to gas sensors and more particularly to a gas sensor in which single crystal SnO micro-disks form the sensing element.

The increase in harmful gas emissions and the resultant threat to public health, particularly in urban environments, has stimulated research aimed at the development of highly sensitive and selective gas sensors suitable for air-quality monitoring [1]. $NO_x$, CO, $H_2S$ are considered particularly harmful to public health, even at low concentrations, given their negative impact on the human respiratory system [2,3]. Detection of these pollutant gases at ppm and ppb levels, with high sensitivity and selectivity, remains a major challenge [4]. While there are a number of means for detecting gases based on optical, gravimetric and electrical approaches, those based on monitoring changes in resistance of semiconducting oxides upon surface adsorption/desorption of gases (chemoresistance) offer key advantages including low cost processing, simple design and measurement, coupled with relatively high sensitivity [5,6,7,8,9].

$SnO_2$ has been the most highly investigated material in this class of sensors [10]. This research has included investigation of different fabrication approaches to form thin films[11], nano [12,13,14], mesoporous [15], and macroporous structures[16,17], as well as the impact of various catalysts and dopants on sensor response [18,19,20]. To achieve higher sensitivity and selectivity, more complex multilayered and metal functionalized structures based on $SnO_2$ have been reported [21,22,23]. Despite these efforts, it has been difficult to obtain simple devices which combine high sensitivity and selectivity with long-term stability.

SUMMARY OF THE INVENTION

The present invention is a gas sensor including a single crystalline SnO disk and circuitry for measuring electrical resistance of the disk, whereby change in resistance indicates adsorption of a gas on the disk's surface. It is preferred that the disks have a diameter in the range of approximately 100 nm to 100 μm. It is also preferred that the SnO disks have a [001] plane exposed to the gas. The sensor of the invention is particularly sensitive to detecting the presence of $NO_2$.

DESCRIPTION OF THE PREFERRED EMBODIMENT

While $SnO_2$ is one of most studied materials for gas sensors applications, to the best of the inventors' knowledge, no sensor response has been reported for tin monoxide, SnO. This lack of research is not surprising given the difficulty in synthesizing this phase and its thermal decomposition at temperatures above 400° C. [24,25]. SnO is reportedly a p-type semiconductor with a tetragonal litharge (alpha lead monoxide) structure, layered in [001] direction and a band gap between 2.5 and 3.0 eV [26,27]. We have synthesized SnO structures by a carbothermal reduction method, displaying both thermal and chemical stability for temperatures below 400° C. [25,28]. In this patent application we disclose the gas sensor properties of SnO disk-like structures. As demonstrated below, these disk-like structures exhibit nearly three orders of magnitude change in resistance upon exposure to nitrogen dioxide gas at temperatures below that typical for oxide chemiresistors. The observation of "Giant Chemo-Resistance" (GCR) in SnO, not dependent on nano-size dimensions, we believe, opens up a new class of promising materials with exceptional gas sensor capabilities and unique surface chemistry.

Disk-like structures were synthesized by a carbothermal reduction method using $SnO_2$ powder (Sigma-Aldrich, 99.9% purity) and carbon black (Union Carbide, >99% purity) in the molar ratio of 1.5:1($SnO_2$:C). Optimized parameters used and details of this synthesis were previously reported [29]. Following synthesis, a dark wool-like material was removed from the inner walls of the alumina tube which had been maintained at a temperature between 350 and 450° C. Both SnO nanobelts and disk-like structures were obtained in this synthesis, but it was possible to separate them by a sedimentation process in isopropyl alcohol. The main focus of this work is on the sedimented material (i.e., the micro-disks) which was separated and dried at 50° C.

The morphological characteristics of the disk-like structures were examined by field emission scanning electron microscopy (FEG-SEM; JEOL, JSM-7500F). The phase and the crystallinity of the disk-like structures were studied by X-ray diffraction (XRD; Shimadzu, XRD 6000) using Cu Kα radiation and transmission electron microscopy (TEM; Philips, CM200) operated at 200 kV. Specific surface area was determined by the Brunauer-Emmett-Teller method (BET; Micromeritics instrument, ASAP 2000) under $N_2$ adsorption/desorption experiments [30]. For the gas sensing measurements, the SnO, collected from the sedimentation process, was dispersed in isopropyl alcohol with the aid of an ultrasonic cleaner. This was followed by dripping the suspension directly onto alumina substrates coated with interdigitated platinum electrode arrays (100 μm Pt fingers spaced 200 μm apart). The substrates were then heated to 100° C. for 15 min to evaporate the solvent. Gas sensing tests were carried out by monitoring changes in resistance (using an HP34970A data acquisition switch unit) during cyclic exposure to different concentrations of $NO_2$ (between 1 and 100 ppm) and $H_2$, $CH_4$ and CO (10 to 500 ppm) diluted in dry air (baseline gas). For this purpose, certified pre-mixed gas mixtures, containing a trace of the test gases diluted in dry air [$NO_2$ (100 ppm) and $H_2$, $CH_4$ and CO (1000 ppm)] (Air Gas) were mixed with clean dry air, using mass flow controllers (MKS). The total gas flow rate (test plus balance gas) was maintained constant (200 sccm) during all tests. The sensor test devices were equilibrated in dry air for 12 h at each temperature before the beginning of each gas sensor measurement to insure a stable and reproducible baseline resistance. Gas sensor measurements were performed in the range from 100 to 300° C. with steps of 50° C. and the sensor signal was defined as $R_{gas}/R_{air}$ for oxidizing gases and as $R_{air}/R_{gas}$ for reducing gases, where $R_{air}$ is the material resistance in air atmosphere and $R_{gas}$ is the material resistance under the analyte gas presence.

In order to study the disks' chemical stability during sensor test measurements, in situ X-ray Absorption Near Edge Spectroscopy (XANES) at the L-edge of Sn was performed during a simulated sensor test at the Brazilian Synchrotron Laboratory. To prepare the sample for XANES analysis, 2 mg of SnO disks were mixed with 50 mg of boron nitrite (BN) in an agate mortar. The powder was then pressed in a 12 mm diameter pellet at 8 MPa. The sample was mounted on a sample holder specially designed for in situ XANES measurements at high temperature, which was then introduced in a quartz tube furnace. XANES measurements were performed from 3900 to 4050 keV with sample maintained at 200° C. (best sensor response temperature). After reaching 200° C. under a $N_2$ gas flux of 100 sccm, the sample was stabilized for 3 h following which the first spectrum was taken. The $N_2$ was then substituted by dry air also at a flow rate of 100 sccm and another spectrum was taken after 30 min. Finally, the gas was switched back to pure $N_2$ and a final spectrum was taken after 1 h. The spectrum of a $SnO_2$ standard sample was also taken for comparison.

Figure 1A:
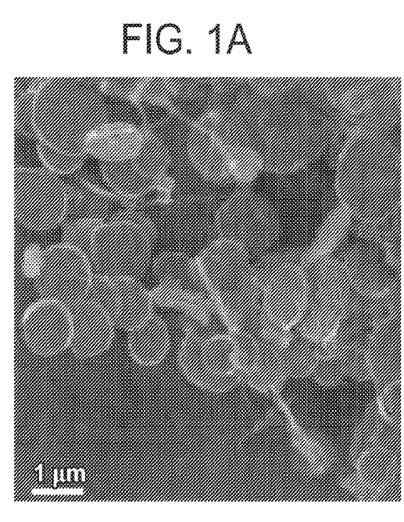
FIG. 1a is a Field Emission gun scanning electron microscope (FEG-SCM) image of disks present in collected material after a sedimentation process.
Figure 1B:
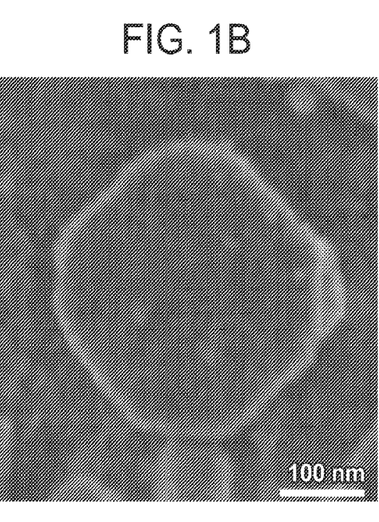
FIG. 1b are high magnification images of isolated disks showing octagon-like disks.
Figure 1C:
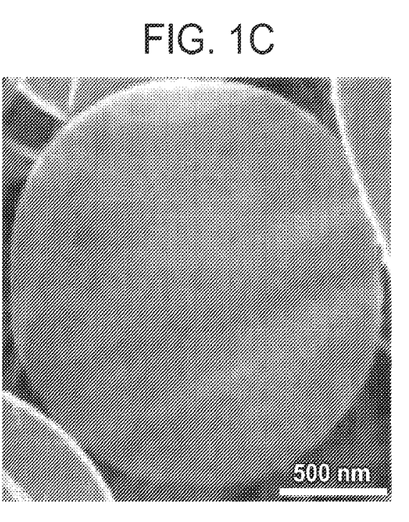
FIG. 1c is a high magnification image of isolated disks having a rounded shape.

FIG. 1 presents FEG-SEM images of the collected material, following separation by sedimentation, showing it to be predominantly composed of disk-like structures with flat and smooth surfaces. These disks have diameters ranging from about 100 nm up to dozens of micrometers. The smaller disks (in general, disks less than 1 μm diameter—FIG. 1b) exhibit an octagon-like faceted shape, while the larger disks are nearly perfectly circular in shape (FIG. 1c). Most disks have diameters greater than 1 μm and these structures are similar to those reported previously in the literature [24,28].

Figure 2A:
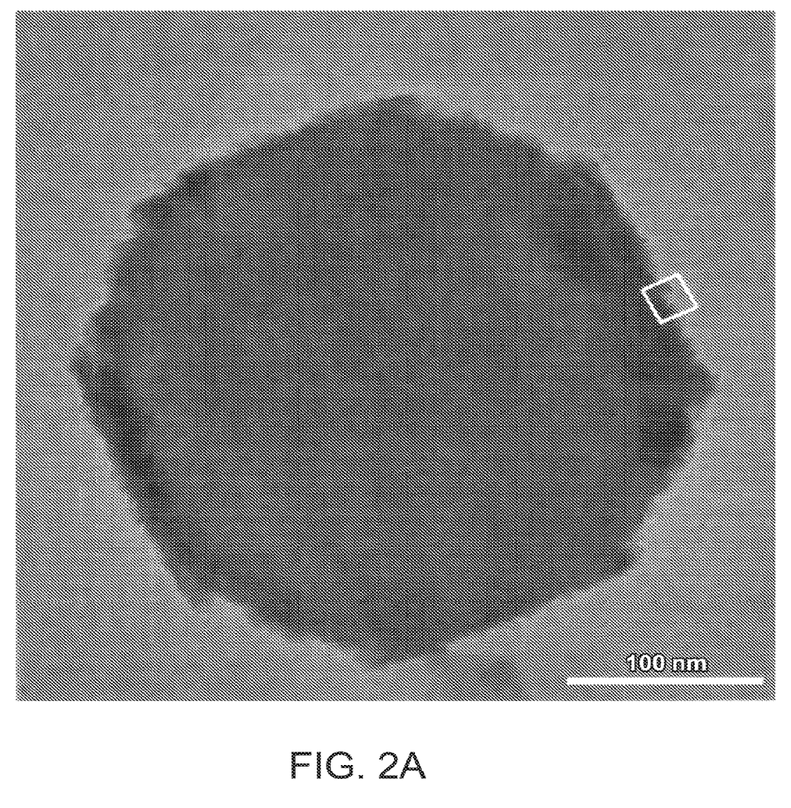
FIG. 2a is a Transmission electron microscopy (TEM) image of a typical faceted disk.
Figure 2B:
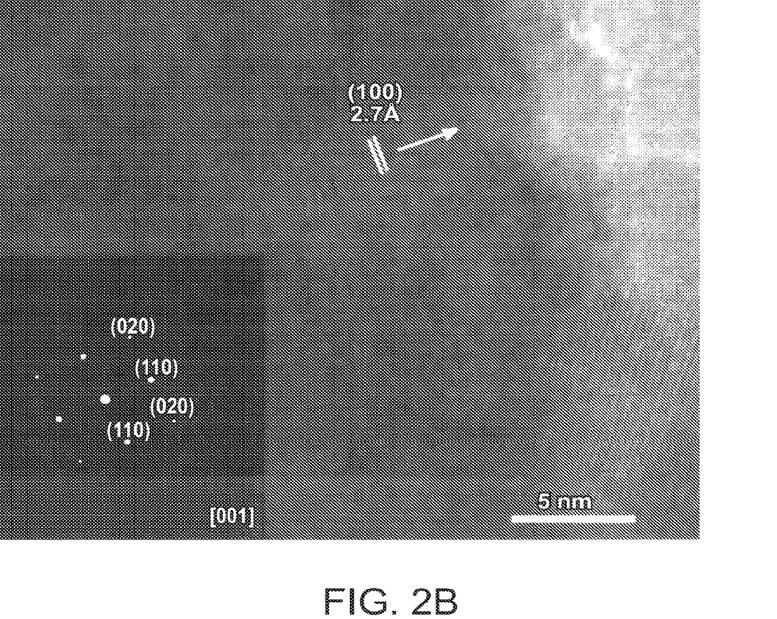
FIG. 2b is a High resolution transmission electron microscopy (HRTEM) image of the white square area in FIG. 2a. The inset is the SAD pattern of the faceted disk.

FIG. 2a shows a low-magnification TEM image of a disk with diameter of about 200 nm and faceted shape. The inset in FIG. 2b presents the SAD pattern of this disk and the isolated spots obtained are typical of single crystalline materials. All of the spots in the SAD pattern can be indexed by the litharge structure of SnO (tetragonal) (JCPDS card #6-395), agreeing with XRD results (not shown here). FIG. 2b also shows an HRTEM image of the disk, confirming that each disk is single crystalline. Occasionally, misoriented particles can be found at the disks' extremities. The inter-planar distance shown in FIG. 2b is 0.27±0.01 nm, related to the (110) planes of the tetragonal structure of SnO, as observed by SAD. Combining SAD and HRTEM results, it was possible to affirm that the larger facets are {110} planes while the smaller ones are {100} planes, which is the same orientation observed by Dai et al.[24]. Moreover, the larger faces of the disks must be the (001) planes, which is perpendicular to the zone axis of the diffraction pattern.

Figure 3:
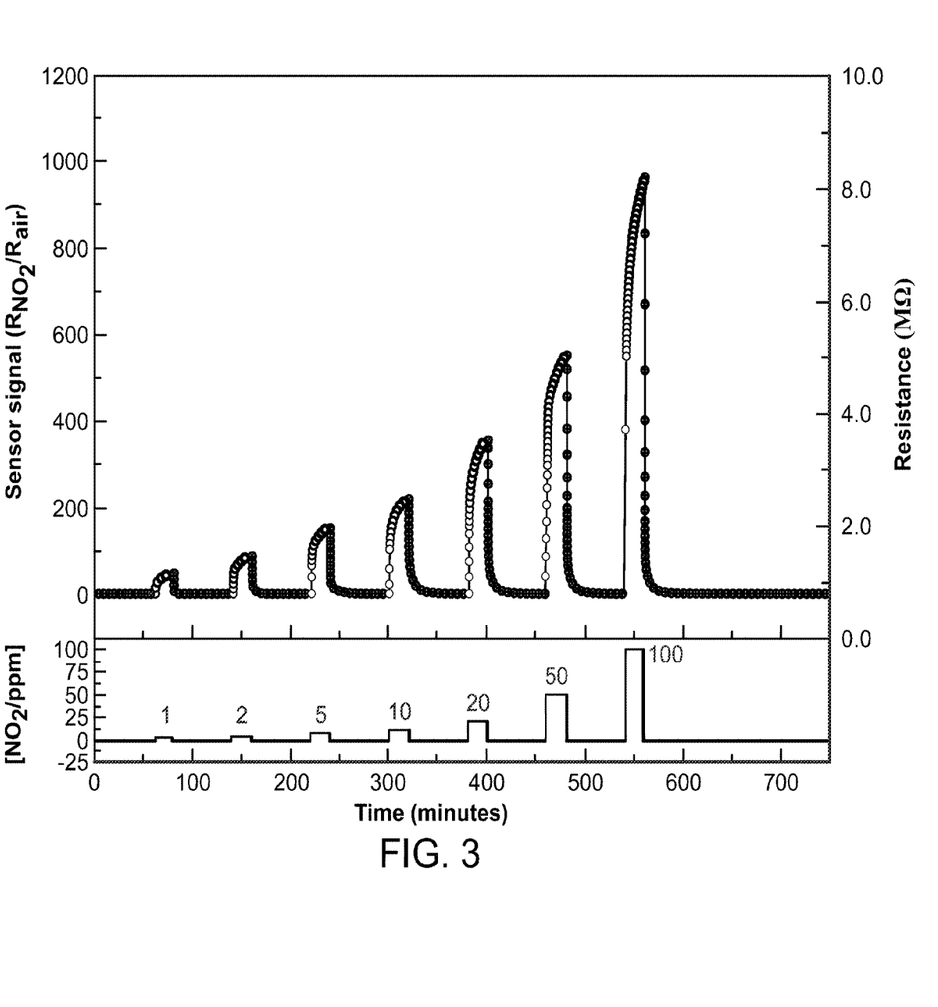
FIG. 3 is a graph of sensor signal versus time of the disk-like structures during cyclic exposure to 20-minute $NO_2$ pulses with increasing concentrations at 200° C.

Typical gas response measurements ($R_{(NO2)}/R_{(air)}$) taken at 200° C., as a function of time for periodic pulses of gases containing $NO_2$ ranging from 1 to 100 ppm, each pulse lasting 20 min, are shown in FIG. 3. The sensor based on SnO disk-like structures exhibited a remarkably strong response when exposure to $NO_2$ with an approximately 50-fold increase in resistance when exposed to 1 ppm $NO_2$ and nearly a 3 orders of magnitude response to 100 ppm $NO_2$. Given the exceptionally high sensitivities observed here, in combination with the fact that this is achieved without need for nano-structuring the material down to the 10 nm regime (see discussion below) and the chemosorption phenomenon nature related to it, we label this response "Giant Chemo-Resistance" (GCR).

For all levels of $NO_2$, the resistance (Rgas) initially increases abruptly when exposed to the analyte gas, followed by an asymptotic change to the steady state with a similar behavior, but slower, observed for the recovery process. This is a typical n-type semiconductor sensor response, although SnO has been reported previously to be a p-type material [26,27]. Clearly, a wide band gap semiconductor such as SnO (Eg >2.5 eV) can be either n or p type, depending on the doping or redox level. Given that the SnO investigated in this study was synthesized by a carbothermal reduction method, it is not surprising that these SnO specimens may be more oxygen deficient than those reported earlier and thus exhibiting n-type behavior. Thermopower and Hall effect studies are planned to determine the carrier density. The sensor response to IOU ppm $NO_2$ versus temperature is shown plotted in FIG. 4, clearly demonstrating that the optimum operating temperature with respect to sensitivity is in the range of 200° C. This is presumably a consequence of the competition between slow gas adsorption kinetics at lower temperatures and enhanced desorption at higher temperatures [31].

Figure 5:
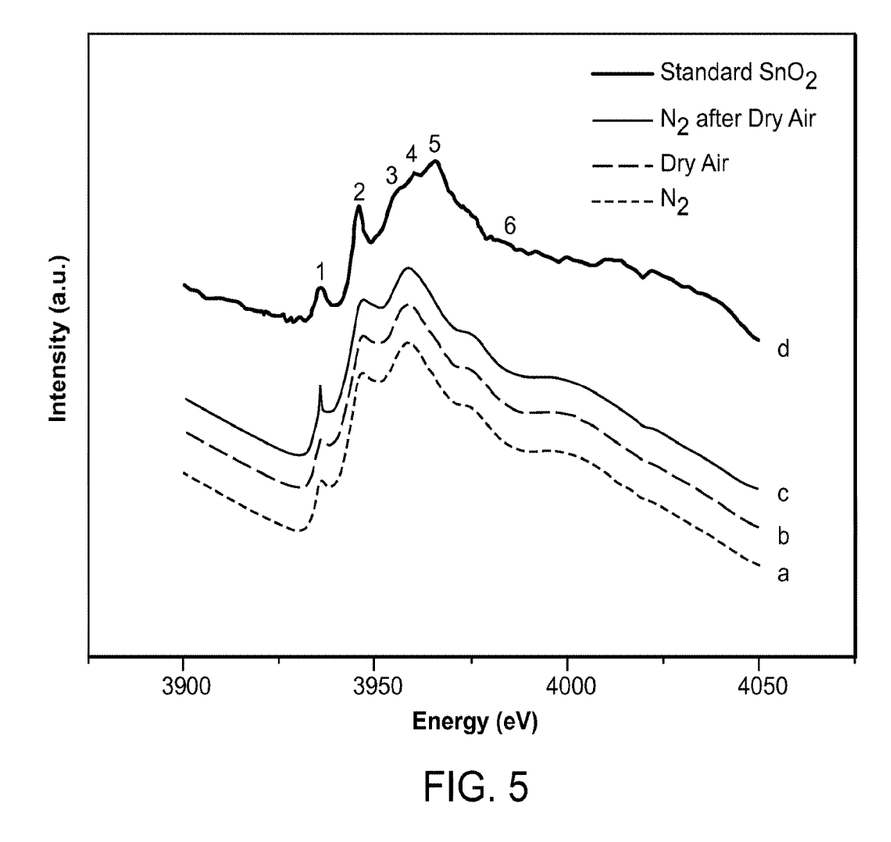
FIG. 5 constitutes graphs of intensity versus energy for X-ray Absorption Near Edge Structure (XANES) spectra for the SnO disks during sensor test simulation at 200° C. Curve a shows measurements performed in $N_2$ after three hours of stabilization. Curve b shows dry air inserted into the chamber followed by $N_2$ again. Curve d shows a standard $SnO_2$ spectrum for comparison.

To study the oxidation state and the chemical stability of disks under different atmospheres at 200° C., XANES measurements were performed under in situ conditions simulating the sensor test measurements. If any variation in the tin oxidation state should occur, a change in XANES spectrum would be observed. Curve a in FIG. 5 shows the XANES spectrum obtained for the sample after 3 h stabilization in pure $N_2$ flux. It has four main absorption peaks, labeled as i, ii, iii and iv, characteristic of the SnO material spectrum [32], thereby confirming the +2 oxidation state of Sn in the micro disks. Comparing this result to the $SnO_2$ standard shown by curve d in FIG. 5, it is clear that the $SnO_2$ signature (broad peak labeled 3,4,5) related to the $2p_{3/2} \rightarrow 6d$ transition, is not present in the XANES spectrum obtained for the SnO disks. Curve b in FIG. 5 shows the XANES spectrum for the SnO disk sample following a 30 min exposure to dry air atmosphere while curve c in FIG. 5 displays the spectrum obtained after 1 h stabilization in pure $N_2$ following the dry air exposure. No change in the spectrum occurs for the SnO sample using either inert or oxidizing atmospheres, indicating good chemical stability for the SnO disk-like structures. The stability against oxidation of SnO to $SnO_2$ at 200° C. was expected given that the observed degradation of SnO at about 400° C. is not an oxidation process, but a thermal activated decomposition process [25].

The sensor signal was found to follow a power law dependence on gas concentration of the form $R \propto p^\beta_{NO2}$ with $\beta$ in this case taking on the value of 0.64. Assuming that this dependence continues to hold to lower $NO_2$ concentrations, a sensor response of ~13 is estimated for an exposure to 100 ppb of $NO_2$ [9]. This easily satisfies the National Ambient Air Quality Standards (NAAQS) requirement of being able to detect 100 ppb per hour, the standard for public health protection set by the U.S. Environmental Protection Agency [33]. It is important to reiterate that this outstanding response was obtained at 200° C., well below the phase transition temperature observed for disk-like structures, therefore insuring stable operation [25]. Furthermore, given the micron rather than nanometer dimensions of these disks, their morphology should be less susceptible to coarsening with time and thereby less likely to exhibit short term aging affects. Moreover, the level of sensitivity to $NO_2$ obtained here is one of the highest reported for catalyst-free tin-based chemiresistors. Few other GCR response reports have been published using catalyst-free $SnO_2$ systems [11,34].

Figure 4:
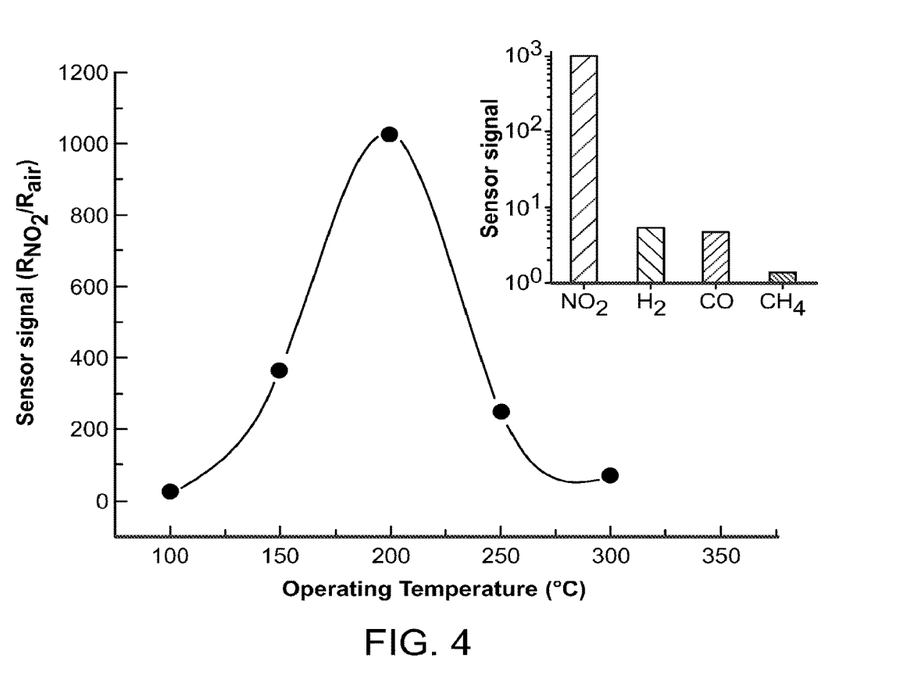
FIG. 4 is a graph of sensor signal against operating temperature for the SnO disk-like structures at 100 PPM $NO_2$ in dry air. The inset shows the sensor signal at 100 PPM of $NO_2$, $H_2$, CO, and $CH_4$ at 200° C.

Gas measurements were also performed to investigate the selectivity of SnO disk-like structures to $NO_2$ versus other potential interferents. The sensor response for 100 ppm of $NO_2$, $H_2$, CO, and $CH_4$ in air at 200° C. is shown in the inset of FIG. 4. The sensor response was more than 200-fold larger for $NO_2$ than for $H_2$ and CO and nearly 1000-fold larger than to $CH_4$, demonstrating the remarkably high selectivity to $NO_2$ relative to these other common interference gases [21,35].

Gas sensor performance is highly influenced by surface area, with larger surface area leading to higher sensitivity [36,37]. In the present case, Brunauer-Emmett-Teller (BET) measurements shows a specific surface area of 8.0 $m^2 g^{-1}$, which cannot explain the giant gas response observed for the SnO disk-like structures. Since the reports of Xu et al. in 1991 [38], showing markedly enhanced sensitivity of $SnO_2$ to CO and $H_2$ gases, as the dimensions of the $SnO_2$ particles decreased below 20-50 nm, many further reports of enhanced sensitivity of nanodimensioned metal oxide chemiresistive sensors have been reported [39,40]. These empirical observations were successfully modeled by Rothschild et al. [41] who took into account the unique characteristics of space charge regions in nanocrystalline semiconductors. This model accounts for the fact that when the radius of the grains, or the thickness of the film becomes smaller than the Debye length, typically on the order of 10 nm, the space charge regions generated at the crystallite or film surfaces overlap such that the entire volume of the crystallite or film becomes depleted of free charge carriers, leading to a much stronger modulation of resistance by adsorption of gases. While similar Debye lengths are calculated for SnO ($\lambda_{D(SnO)}$~7-20 nm at 200° C., depending on carrier density), the much larger dimensions of the largely single crystalline SnO disk structures studied here, typically between 70 and 250 nm thick, suggest that charge carrier depletion across the whole thickness of the disks cannot be responsible for the GCR sensor response observed here.

Recently, it was demonstrated that the sensitivity of $SnO_2$-based sensors can be improved by exposing specific facets at the surface [12] i.e., specific crystallographic planes can lead to higher sensitivity due to their high chemical activity. As previously reported [24] and discussed further in this work, the SnO disks studied here are bi-dimensional structures with large (001) exposed surface planes. For litharge structures, it is known that the (001) plane exhibits a high fraction of electronic lone pairs [42,43].

According to recent DFT calculations, the sterically active lone pair, normally ascribed to the filled Sn $5s^2$ orbital, shows instead that the states responsible for the asymmetric Sn electron distribution are due to the coupling of unfilled Sn(5p) with the antibonding combination arising from interaction of Sn(5d) and O(2p) orbitals. These lone pairs, with relatively high energy states at the top of the valence band, make the transfer of electrons to the adsorbed molecules more favorable [44]. The high density of such lone pair orbitals in the (001) surface plane may then explain the enhanced capacity of SnO to absorb oxidizing species such as $NO_2$, as well as its strong selectivity to oxidizing vs reducing gases.

The single crystalline SnO micro-disks disclosed herein, synthesized by a carbothermal reduction process, exhibited a nearly 1000-fold increase in resistance upon exposure to 100 ppm of $NO_2$ without addition of catalysts or dopants nor the existence of nano-sized dimensions. Moreover, the SnO displayed a greater than 100-fold selectivity to $NO_2$ over potential interferents including CO, $H_2$ and $CH_4$. The high sensor signal and exceptional selectivity for this novel sensor material are attributed to the existence of a high density of active lone pair electrons on the exposed (001) planes of the single crystalline SnO disks. This, thereby, identifies new means, not utilizing nano-dimensions, to achieve high gas sensitivity.

Figure 6:
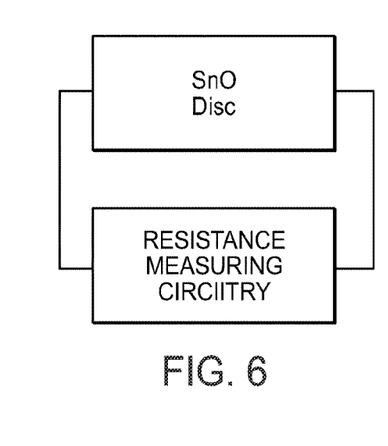
FIG. 6 is a schematic illustration of a gas sensor using a SnO disk as the sensor element.

FIG. 6 is a schematic gas sensor in which a SnO disk is in a circuit to measure its electrical resistance. Resistance changes indicate the presence of a gas such as $NO_2$. The sensor may be operated either by maintaining a fixed voltage and measuring changes in current during gas exposure or maintaining a constant current and measuring the change in voltage.

It is recognized that modifications and variations of the present invention will be apparent to those of ordinary skill in the art and it is intended that all such modifications and variations be included within the scope of the appended claims.

The numbers in brackets refer to the references listed herein. The contents of all these references are incorporated herein by reference.

REFERENCES

[1] N. O. Korolkoff, Survey of toxic gas sensors and monitoring systems, Solid State Tech. 32 (1989) 49-64.

[2] G. Weinmayr, E. Romeo, M. Sario, S. K. Weiland, F. Forastiere, Short-Term effects of PM10 and $NO_2$ on respiratory health among children with asthma or asthma-like symptoms: a systematic review and meta-analysis, Environmental Health Perspectives 118 (2010) 449-457.

[3] C. Pijolat, C. Pupier, M. Sauvan, G. Toumier, R. Lalauze, Gas detection for automotive pollution control, Sens. Actuators, B: Chem. 59 (1999) 195-202.

[4] N. Yamazoe, N. Miura, Environmental gas-sensing, Sens. Actuators, B: Chem. 20 (1994) 95-102.

[5] L. Zhang, J. Zhao, H. Lu, L. Li, J. Zheng, H. Li, Z. Zhu, Facile synthesis and ultrahigh ethanol response of hierarchically porous ZnO nanosheets, Sens. Actuators, B: Chem. 161 (2012) 209-215.

[6] S. J. Kim, I. S. Hwang, C. W. Na, I. D. Kim, Y. C. Kang, J. H. Lee, Ultrasensitive and selective $C_2H_5OH$ sensors using Rh-loaded $In_2O_3$ hollow spheres, J. Mat. Chem. 21 (2011) 18560-18567.

[7] A. Gurlo, M. Ivanovskaya, N. Barsan, M. Schweizer-Berberich, U. Weimar, W. Gopel, A. Dieguez, Grain size control in nanocrystalline $In_2O_3$ semiconductor gas sensors, Sens. Actuators, B: Chem. 44 (1997) 327-333.

[8] J. Tamaki, T. Hashishin, Y. Uno, D. V. Dao, S. Sugiyama, Ultrahigh-sensitive $WO_3$ nanosensor with interdigitated Au nano-electrode for $NO_2$ detection, Sens. Actuators, B: Chem. 132 (2008) 234-238.

[9] I.-D. Kim, A. Rothschild, B. H. Lee, D. Y. Kim, S. M. Jo, H. L. Tuller, Ultrasensitive chemiresistors based on electrospun $TiO_2$ nanofibers, Nano Lett. 6 (2006) 2009-2013.

[10] D. D. Vuong, G. Sakai, K. Shimanoe, N. Yamazoe, Hydrogen sulfide gas sensing properties of thin films derived from $SnO_2$ sols different in grain size, Sens. Actuators, B: Chem. 105 (2005) 437-442.

[11] X. Han, M. Jin, S. Xie, Q. Kuang, Z. Jiang, Y. Jiang, Z. Xie, L. Zheng, Synthesis of tin dioxide octahedral nanoparticles with exposed high-energy {221} facets and enhanced gas-sensing properties, Angew. Chem. Int. Ed. 48 (2009) 9180-9183.

[12] H.-C. Chiu, C.-S. Yeh, Hydrothermal synthesis of $SnO_2$ nanoparticles and their gas-sensing of alcohol, J. Phys. Chem. C 111 (2007) 7256-7259.

[13] Y. Kwak, J. Wang, S. Meang, G.-H. Kim, Hydrogen sensing properties of dielectrophoretically assembled $SnO_2$ nanoparticles on CMOS-compatible micro-hotplates, Nanotechnology 22 (2011) 445501.

[14] T. Hyodo, N. Nishida, Y. Shimizu, M. Egashira, Preparation and gas-sensing properties of thermally stable mesoporous $SnO_2$, Sens. Actuators, B: Chem. 83 (2002) 209-215.

[15] N. G. Cho, D. J. Yang, M. J. Jin, H. G. Kim, H. L. Tuller, L-D. Kim, Highly sensitive $SnO_2$ hollow nanofiber-based $NO_2$ gas sensors, Sens. Actuators, B: Chem. 160 (2011) 1468-1472.

[16] T. Hyodo, K. Sasahara, Y. Shimizu, M. Egashira, Preparation of macroporous $SnO_2$ films using PMMA microspheres and their sensing properties to NOx and $H_2$, Sens. Actuators, B: Chem. 106 (2005) 580-590.

[17] J. Zhang, X. H. Liu, S. H. Wu, M. J. Xu, X. Z. Guo, S. R. Wang, Au nanoparticle-decorated porous $SnO_2$ hollow spheres: a new model for a chemical sensor, J. Mat. Chem. 20 (2010) 6453-6459.

[18] J.-A. Park, J. Moon, S.-J. Lee, S. H. Kim, H. Y. Chu, T. Zyung, $SnO_2$—ZnO hybrid nanofibers-based highly sensitive nitrogen dioxides sensor, Sens. Actuators, B: Chem. 145 (2010) 592-595.

[19] N. G. Cho, G. C. Whitfield, D. J. Yang, H.-G. Kim, H. L. Tuller, I.-D. Kim, Facile synthesis of Pt-functionalized $SnO_2$ hollow hemispheres and their gas sensing properties, J. Electrochem. Soc. 157 (2010) J435-J439.

[20] D.-J. Yang, I. Kamienchick, D. Y. Youn, A. Rothschild, I.-D. Kim, Ultrasensitive and highly selective gas sensors based on electrospun $SnO_2$ nanofibers modified by Pd loading Adv. Funct. Mater. 20 (2010) 4258-4264.

[21] Z. Ling, C. Leach, R. Freer, $NO_2$ sensitivity of a heterojunction sensor based on $WO_3$ and doped $SnO_2$, J. Eur. Ceram. Soc. 23 (2003) 1881-1891.

[22] M. K. Verma, V. Gupta, A highly sensitive $SnO_2$—CuO multilayered sensor structure for detection of $H_2S$ gas, Sens. Actuators, B: Chem. 166 (2012) 378-385.

[23] Z. R. Dai, Z. W. Pan, Z. L. Wang, Growth and structure evolution of novel tin oxide diskettes, J. Am. Chem. Soc. 124 (2002) 8673-8680.

[24] M. O. Orlandi, A. J. Ramirez, E. R. Leite, E. Longo, Morphological evolution of tin oxide nanobelts after phase transition, Cryst. Growth Des. 8 (2008) 1067-1072.

[25] M. Batzil, U. Diebold, The surface and materials science of tin oxide, Progress in Surf. Sci. 79 (2005) 45-154.

[26] Y. Ogo, H. Hiramatsu, K. Nomura, H. Yanagi, T. Kamiya, M. Hirano, H. Hosono, p-channel thin-film transistor using p-type oxide semiconductor, SnO, Appl. Phys. Lett. 93 (2009) 032113.

[27] M. O. Orlandi, E. R. Leite, R. Aguiar, J. Bettini, E. Longo, Growth of SnO nanobelts and dendrites by a self-catalytic VLS process, J. Phys. Chem. B 110 (2006) 6621-6625.

[28] P. H. Suman, M. O. Orlandi, Influence of processing parameters on nanomaterials synthesis efficiency by a carbothermal reduction process, J. Nanoparticle Research 13 (2011) 2081-2088.

[29] S. Brunauer, P. H. Emmett; E. Teller. Adsorption of gases in multimolecular layers, J. Am. Chem. Soc. 60 (1938) 309-319.

[30] J. L. G. Fierro, Metal Oxide Chemistry and Applications, CRC Press, Boca Raton, Fla., 2006.

[31] H. W. Ha and S. J. Hwang. Improvement of electrochemical performance of tin dioxide negative electrode materials upon cobalt substitution, Electrochimica Acta 55 (2010) 2841-2847.

[32] U.S. Environmental Protection Agency: National Ambient Air Quality Standards (NAAQS). http://www.epa.gov/air/criteria.html.

[33] M. Epifani, J. D. Prades, E. Comini, E. Pellicer, M. Avella, P. Siciliano, G. Faglia, A. Cirera, R. Scotti, F. Morazzoni, J. R. Morante. The role of surface oxygen vacancies in the $NO_2$ sensing properties of $SnO_2$ nanocrystals, J. Phys. Chem. C 112 (2008) 19540-19546.

[34] Y.-E. Chang, D.-Y. Youn, G. Ankonina, D.-J. Yang, H.-G. Kim, A. Rothschild, I.-D. Kim, Fabrication and gas sensing properties of hollow $SnO_2$ hemispheres, Chem. Commun. 27 (2009) 4019-4021.

[35] K. Sahner, H. Tuller, Novel deposition techniques for metal oxide: prospects for gas sensing, J. Electroceram. 24 (2010) 177-199.

[36] N. Barsan, U. Weimar, Conduction model of metal oxide gas sensors, J. Electroceram. 7 (2001) 143-167.

[37] C. Xu, J. Tamaki, N. Miura, and N. Yamazoe, Grain-size effects on gas sensitivity of porous $SnO_2$-based elements, Sens. Actuators B: Chem. 3 (1991) 147-155.

[38] H. Keskinen, A. Tricoli, M. Marjamäki, J. M. Mäkelä, S. E. Pratsinis, Size-selected agglomerates of $SnO_2$ nanoparticles as gas sensors, J. Appl. Phys. 106 (2009) 084316.

[39] L. Shi and H. Lin, Preparation of band gap tunable $SnO_2$ nanotubes and their ethanol sensing properties, Langmuir 27 (2011) 3977-3981.

[40] A. Rothschild and Y. Komem, The effect of grain size on the sensitivity of nanocrystalline metal-oxide gas sensors, J. Appl. Phys. 95 (2004) 6374-6380.

[41] D. Le Bellac, J. M. Kiat, P. Garnier, Electronic lone pair localization and electrostatic energy calculations: application to α-PbO, SnO, $Pb_{1-x}(TiO)_xO$, $Pb_3O_4$, $Pb_3(V,P)_2O_8$, and a BiSrCaCuO-type superconductor, J. Solid State Chem. 114 (1995) 459-468.

[42] A. Walsh, G. W. Watson, Electronic structures of rocksalt, litharge, and herzenbergite SnO by density functional theory, Phys. Rev. B. 70 (2004) 235114.

What is claimed is:

1. Gas sensor comprising:
a single crystalline SnO disk; and
circuitry for measuring electrical resistance of the disk, whereby change in resistance indicates adsorption of a gas on the disk's surface, wherein the SnO disk has a

[001] plane that includes a plurality of a lone pair orbitals that enhances the capacity of the SnO disk to absorb oxidizing species exhibiting both thermal and chemical stability for temperatures below 400° C., the circuitry maintains a fixed voltage and measures the change in current during exposure of the gas onto the SnO disk, or maintains a fixed current and measures the change in voltage during exposure of the gas unto the SnO disk to assess the electrical resistance of the SnO disk.

2. The gas sensor of claim 1 wherein the disk has a diameter in the range of approximately 100 nanometers to 100 μm.

3. The gas sensor of claim 1 wherein the gas is $NO_2$.

* * * * *